United States Patent [19]

Flaton

[11] Patent Number: 4,736,739
[45] Date of Patent: Apr. 12, 1988

[54] PHOTOGRAPHIC SPECIMEN MAT
[75] Inventor: Frank G. Flaton, St. Louis, Mo.
[73] Assignee: Dowd & Dowd, P.C., St. Louis, Mo.
[21] Appl. No.: 816
[22] Filed: Jan. 6, 1987

Related U.S. Application Data

[63] Continuation-in-part of Ser. No. 737,706, May 28, 1985, abandoned.

[51] Int. Cl.[4] .................. A61F 13/00; G01B 11/24
[52] U.S. Cl. .................. 128/132 D; 33/121; 356/397
[58] Field of Search ............ 128/132 D, 453, 463, 128/464, 644; 350/535; 354/79, 109; 356/397, 379, 421; 33/1 B, 121

[56] References Cited

U.S. PATENT DOCUMENTS

| 118,006 | 8/1871 | Foss | 354/354 |
|---|---|---|---|
| 990,832 | 5/1911 | Brandweiner | 355/40 |
| 1,920,259 | 8/1933 | Jackson | 33/1 CC |
| 3,525,330 | 8/1970 | Greene | 128/644 |
| 3,538,912 | 11/1970 | Becker, III | 128/132 D |
| 3,769,895 | 11/1973 | Lucas | 354/292 |
| 3,809,077 | 5/1974 | Hansen | 128/132 D |
| 4,131,998 | 1/1979 | Spears | 33/121 X |
| 4,281,910 | 8/1981 | Takayama | 354/79 X |
| 4,422,759 | 12/1983 | Holman et al. | 356/421 X |
| 4,535,782 | 8/1985 | Zoltan | 356/379 X |

FOREIGN PATENT DOCUMENTS

| 215914 | 11/1909 | Fed. Rep. of Germany | 33/121 |
|---|---|---|---|
| 1803142 | 4/1970 | Fed. Rep. of Germany | 356/397 |

Primary Examiner—Richard T. Stouffer
Attorney, Agent, or Firm—Glenn K. Robbins

[57] ABSTRACT

A mat for surgical specimens and the like. The mat is comprised of an upper and lower layer. The upper layer is comprised of flexible absorbent material upon which a grid is imprinted in order that specimens may be photographed with spatial and size orientation. The absorbent nature of the upper layer provides for absorption of blood or other body fluids. The bottom layer is comprised of a flexible non-porous material to prevent staining of a work surface supporting the mat. The two layers are sealed together to prevent drainage along the interface of the layers.

6 Claims, 2 Drawing Sheets

PHOTOGRAPHIC SPECIMEN MAT

RELATED APPLICATION

This application is a continuation-in-part of my co-pending application Ser. No. 737,706, filed May 28, 1985, now abandoned.

BACKGROUND OF THE INVENTION

In the past the photographing of surgical specimens or the like has been effected by simply placing the specimen on a work surface or upon a towel and photographing the specimen. Such procedure while a simple means of effecting the photographing has caused problems in staining the work surface due to leak through of blood, serum and other body fluids. Further, size and spatial orientation are not provided in the developed photograph. If a reference object is physically placed alongside the specimen to be photographed, complications arise due to the attention required in obtaining the reference object, of proper size, positioning it and the introduction of a non-sterile object to the area.

SUMMARY OF THE INVENTION

By means of this invention there has been provided a flexible mat of two layers which can be used with a top grid imprint to photograph specimens in a clean, simple and efficient manner.

The upper or top layer is comprised of an absorbent or permeable flexible material of plastic or fabric in order to absorb fluids that may be associated with the specimen. The top surface of the upper layer is imprinted with a grid of preselected spacing such as one centimeter squares in order to provide a reference for the size of the specimen being photographed.

The lower or bottom layer is comprised of a flexible material of plastic or the like which is impermeable and serves as a fluid barrier. It is bonded or cemented to the top layer throughout to prevent drainage along the interface of the layers. The lower layer serves to trap or block the absorbed fluids on the top layer and prevent staining the work surface upon which the mat is positioned.

The mat, through its flexible nature, may be provided in roll form in scored or perforated tear lines for ready tearing from the roll or stacked in packs.

The mat may be desirably employed in the photographing of surgical specimens or the like in the operating room as the specimens are removed. Such specimens are often associated with body fluids such as blood, serum or the like. The absorbent nature of the upper layer serves to absorb such fluids while the impermeable bottom layer acts as a fluid barrier to stop the fluids. The printed grid provides a reference for size and space orientation of the specimen being photographed for convenience in subsequent study of the photographed specimen. While reference has been made to photographing of surgical specimens, it will be understood that the mat is of general application and may be employed in other scientific fields for photographing of specimens of one type or another where size orientation or absorption of fluids associated with the specimen is desirable.

The above features are object of this invention. Further objects will appear in the detailed description which follows and will be further apparent to those skilled in the art.

For the purpose of illustration of this invention, a preferred embodiment is shown in the accompanying drawing. It is to be understood that the drawing is for the purpose of example only and that the invention is not limited thereto.

IN THE DRAWING

DESCRIPTION OF THE INVENTION

Figure 1:
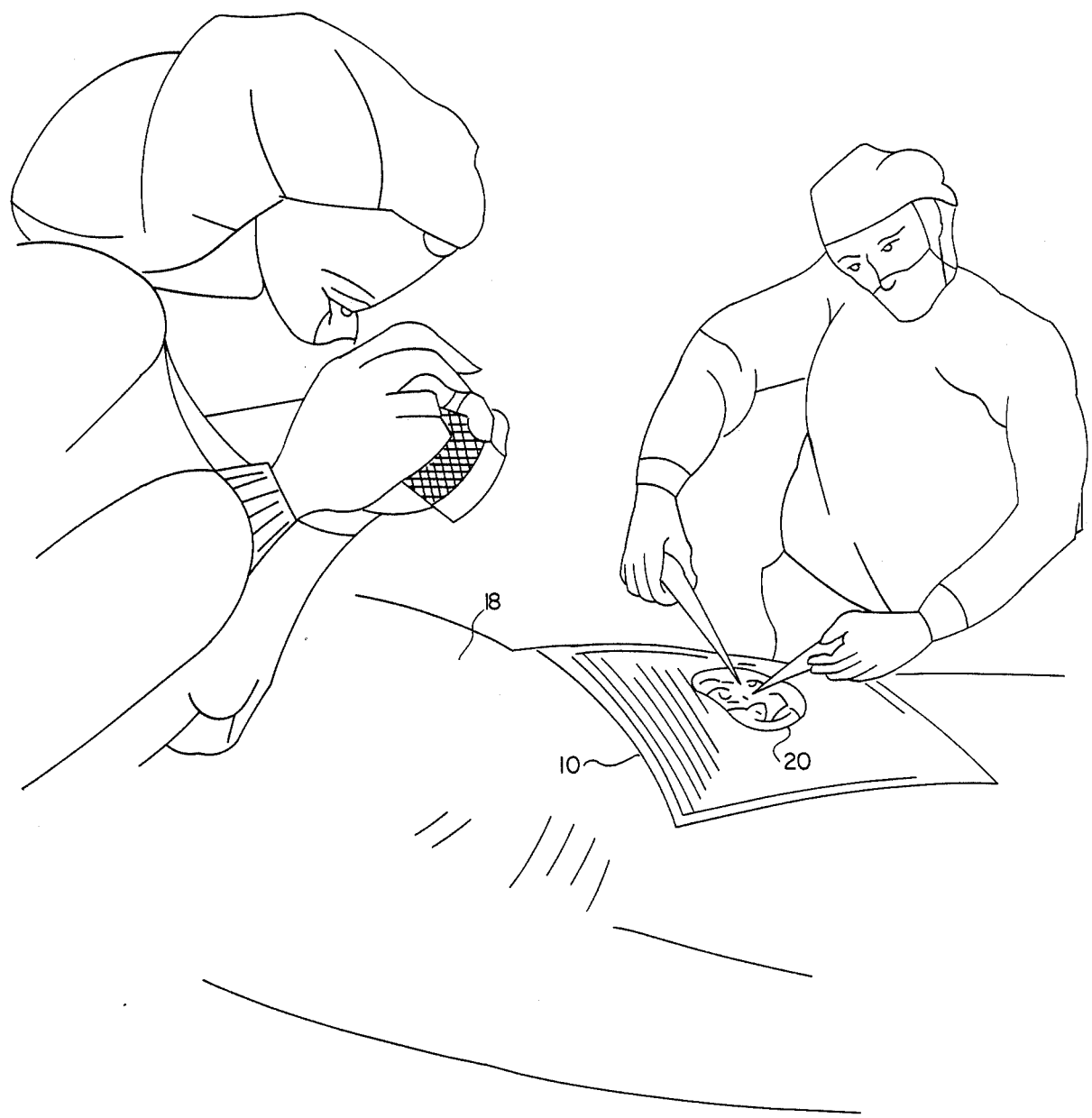
FIG. 1 is a pictorial view of the surgical mat in use in an operating room.

The mat of this invention is generally indicated by the reference numeral 10 in FIGS. 1 through 4. It is comprised of an upper or top layer 12 and a lower or bottom layer 14. The two layers are suitably secured together by a conventional cement or the like.

Figure 3:
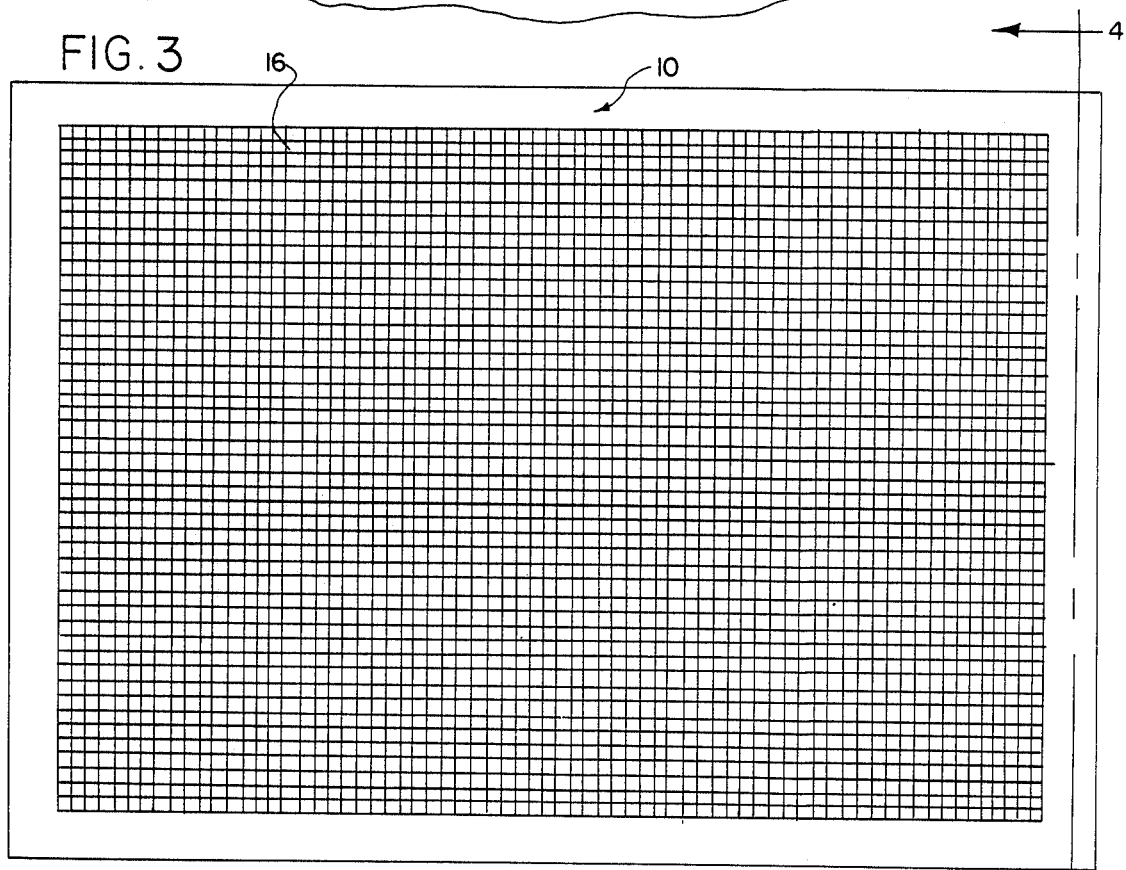
FIG. 3 is a top plan view of the surgical mat.
Figure 4:
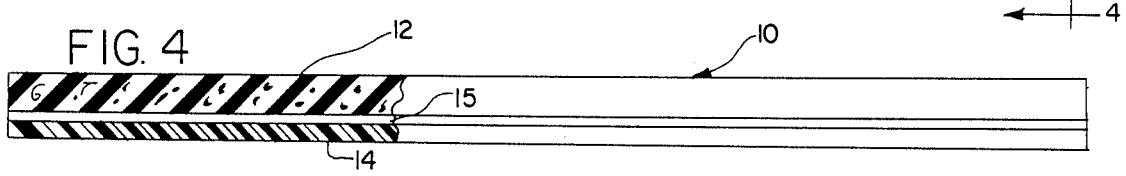
FIG. 4 is a view in section of the mat taken on the line 4—4 of FIG. 3.

The upper layer 12 as best shown in FIGS. 3 and 4 is provided on a top surface with a grid 16. The grid is desirably printed or otherwise provided in one centimeter squares as this is most commonly used in scientific applications. It will be understood that other spacings or graduations may be employed as desired.

The upper layer 12 is comprised of a flexible absorbent permeable material such as porous urethane plastic or the like or a suitable textile fabric. The upper layer as shown in FIG. 4 is somewhat thicker than the bottom layer 14 in order to provide a suitable absorbent holding capacity for any fluids associated with the specimen placed on the mat.

The bottom layer 14 as best shown in FIG. 4 is comprised of a flexible sheet of impermeable material to serve as a fluid barrier. It may be composed of a flexible impermeable plastic such as vinyl or the like.

The upper layer 12 and the bottom layer 14 are bonded together substantially throughout their mating surface such as by an adhesive layer 15 as shown in FIG. 4 or by heat sealing or the like. The adhesive layer provides a continuous bond to prevent draining or channeling of fluid along the interface of the upper and bottom layers. It will be understood that the bonding for economy may also be in concentric rings to provide drainage barriers along the interface of the layers as desired.

The mat in its finished form may be made in any convenient size. For the purpose of example and without limitation, a surface area of 16 inches by 20 inches and a total thickness of ⅛ inch may be desirably employed.

For the purpose of desirability in photographing of the specimen, the top surface of the mat is flat and non-reflective. It may be a complementary color to the specimen being photographed such as blue or flat black. The grid lines are in constrasting color for ready legibility or reference.

The mat may be disposable where employed in sterile environments or reused with washing or cleaning as necessary.

USE

The mat 10 of this invention is very simply employed in photographic applications. The specimen wet or dry is simply placed on the mat and photographed.

The mat is shown in FIG. 1 in use in an operating room. In this figure for the purpose of example, the mat is placed on the torso 18 of a person being operated upon. A large opening 20 is cut in the mat and the mat is placed upon the torso operated upon. In this application the surgeon may place any specimen removed upon the mat and the photographer shown in the figure may photograph the specimen as well as the area of the operation.

The grid on the top layer provides a permanent reference in the photograph to the size of the specimen and the size of the area and internal organs of the torso exposed in the opening of the mat.

Figure 2:
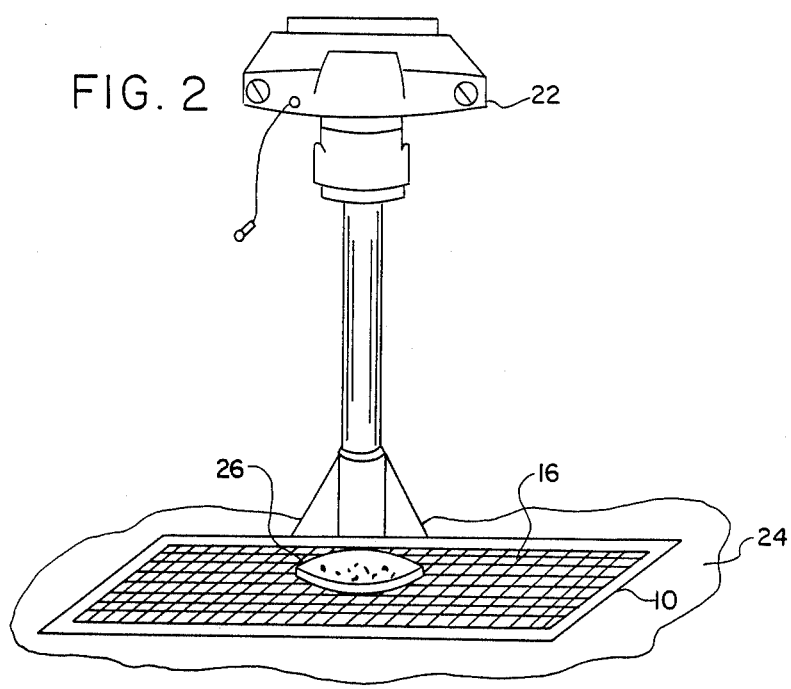
FIG. 2 is a pictorial view of the surgical mat employed in the photographing of a culture dish.

Another application is shown in FIG. 2 in a laboratory or the like. A stationary camera 22 having a work surface 24 is employed to photograph a Petri or culture dish 26 placed upon the mat. Other specimens wet or dry may be similarly photographed with ready size orientation being provided by the grid 16.

The mat may be simply efficiently employed in other applications as will be readily understood. The absorbent and permeable nature of the grid imprinted upper layer and the impermeable fluid barrier nature of the bottom layer serve efficiently to provide specialized application in the photographing or surgical specimens as well as general application to the photographing of a wide variety of specimens or objects of one type or another where fluid absorption and size referencing are desired.

Various changes and modifications may be made within this invention as will be apparent to those skilled in the art. Such changes and modifications are within the scope and teaching of this invention as defined in the claims appended hereto.

What is claimed is:

1. A sheet-like mat for the photographing of specimens, said mat being comprised of an upper layer and a lower layer, the bottom of said upper layer and the top of said lower layer being mating surfaces in contact with one another, said upper layer being constructed of fluid absorbent permeable material for absorption of any fluid draining from the specimens and a top surface provided with rectangular grid lines readily distinguishable from the remainder of said top surface, said grid lines physically incorporated into said top surface and having a preselected spacing for size referencing of the specimens and said lower layer being constructed of fluid impermeable material to provide a fluid barrier to fluid absorbed in the upper layer, said upper and lower layers being bonded together substantially throughout their mating surfaces with overlying and mating contact with one another to prevent drainage of fluid along the mating surfaces of the layers and to trap absorbed fluid on the upper layer.

2. The mat of claim 1 in which the upper layer is substantially thicker than the lower layer to provide a substantial fluid absorbing capacity.

3. The mat of claim 2 in which both the upper and lower layers are flexible and have the capacity to drape over a supporting surface and the upper layer comprises an absorbent fluid permeable plastic material and the lower layer comprises a fluid impermeable plastic material.

4. The mat of claim 1 in which both the upper and lower layers are flexible and have the capacity to drape over a supporting surface.

5. The mat of claim 1 in which the upper layer comprises an absorbent fluid permeable plastic material and the lower layer comprises a fluid impermeable plastic material.

6. The mat of claim 1 in which the top surface of the mat is flat and non-reflective to minimize glare when photographed.

* * * * *